United States Patent [19]

Ganguly et al.

[11] 4,366,309
[45] Dec. 28, 1982

[54] DERIVATIVES OF ANTIBIOTIC AR-5 COMPONENTS

[75] Inventors: Ashit K. Ganguly, Upper Montclair; Yi-Tsung Liu, Parsippany; Olga Sarre, Verona; Robert Jaret, Livingston; Doris P. Schumacher, Florham Park, all of N.J.

[73] Assignee: Schering Corporation, Kenilworth, N.J.

[21] Appl. No.: 253,138

[22] Filed: Apr. 13, 1981

Related U.S. Application Data

[63] Continuation-in-part of Ser. No. 130,330, Mar. 14, 1980, abandoned.

[51] Int. Cl.³ .............................................. C07H 17/08
[52] U.S. Cl. ...................................... 536/7.1; 424/180
[58] Field of Search ........................ 536/9, 17 R, 17 C

[56] References Cited

U.S. PATENT DOCUMENTS

| | | | |
|---|---|---|---|
| 3,769,273 | 10/1973 | Massey | 536/17 R |
| 3,853,842 | 12/1974 | Kishi et al. | 536/9 |
| 3,975,372 | 8/1976 | Ganguly et al. | 536/17 R |
| 4,056,616 | 11/1977 | Reimann et al. | 536/17 R |

Primary Examiner—Johnnie R. Brown
Attorney, Agent, or Firm—Gerald S. Rosen; Gerald F. Swiss; Bruce M. Eisen

[57] ABSTRACT

Novel macrolide antibacterial derivatives of the components of the Antibiotic AR-5-complex are disclosed herein. The invention specifically relates to compounds wherein the macrolide ring and/or the two attached sugars are derivatized. Also disclosed are methods for the preparation of the derivatives and methods for the use thereof.

50 Claims, No Drawings

DERIVATIVES OF ANTIBIOTIC AR-5 COMPONENTS

This application is a continuation-in-part of copending application Ser. Number 130,330, filed Mar. 14, 1980, now abandoned.

This invention relates to novel antibacterial agents derived from components of the Antibiotic AR-5 complex. The preparation of the complex is described in U.S. application Ser. No. 93,080, filed November 9, 1979 now U.S. Pat. No. 4,307,085. It is also noted that British Patent publication No. 2,020,647A, published Nov. 21, 1979 appears to disclose the same or quite similar macrolide starting materials.

This application is directed to compounds having the following formulae:

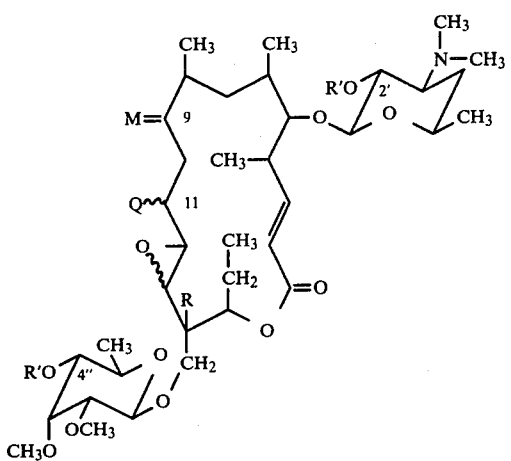

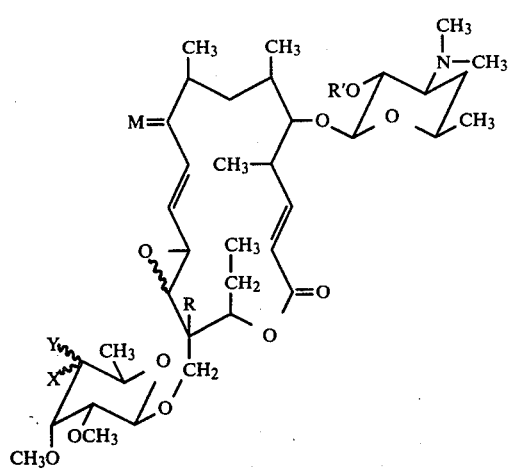

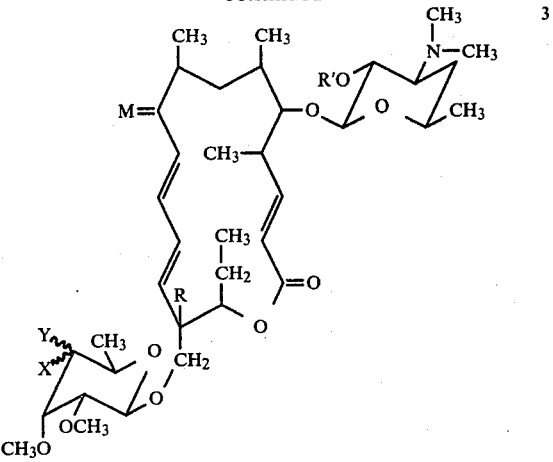

and the pharmaceutically acceptable salts and esters thereof, wherein the wavy line indicates that the substituent may be in any of the possible stereochemical configurations; R is a member of a group consisting of hydrogen and hydroxyl; R' is a member of a group consisting of hydrogen and $C_2$-$C_{18}$ alkanoyl, carbamoyl and thiocarbamoyl; M is a member of the group consisting of oxygen and H, OR'; Q is a member of the group consisting of —NZ and —SZ' wherein —NZ is a member of the group consisting of amino, acylamino, alkylamino, dialkylamino, hydroxyalkylamino, alkylimino or aralkylimino, aminothiocarbonylaminoalkyl, amidinyl, alkylcarboxyamino, ureido, 4-ethyl-2,3-dioxopiperazinocarbonylamino, guanidino, alkylguanidino and an amino acid residue; —SZ' is a member of the group consisting of alkylthio, thioxanthyl, including alkyl, aryl and aralkyl, thioxanthyl, alkylaminoalkythio, arylthio, aralkythio, heterocyclethio, heterocyclealkylthio, heterocyclearalkylthio, heterocyclearylthio, alkylcarboxyalkylthio and sulfur containing amino acid residues, X is a member of the group consisting of hydrogen, OR'epi, mesyloxy, tosyloxy, trifluoromethanesulfonyloxy, halogeno, azido, amino, isocyanato, thioisocyanato, alkylimino, arylimino or aralkylimino, urethano, amidino, guanidino, alkoxyamino, cyclic guanidino when Y is hydrogen; and Y in combination with X is oxygen. R″ and R‴ which may be the same or different are members of the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

The term OR'epi denotes such groups wherein the OR' is epimeric to that of the antibiotics derived for the fermentation of *Micromonospora Polytrata*.

The term "pharmaceutically acceptable salts" refers to non-toxic acid addition salts of the compounds of this invention which are usually prepared by reacting the free base with a suitable organic or inorganic acid. Representative salts include the hydrochloride, hydrobromide, sulfate, bisulfate, acetate, propionate, oxalate, valerate, oleate, palmitate, stearate, laurate, borate, benzoate, lactate, phosphate, tosylate, mesylate, citrate, maleate, fumarate, tartrate, succinate, napsylate, and adamantane carboxylate.

In like manner, the term "pharmaceutically acceptable esters" refers to the non-toxic reaction products formed when an acyl anhydride, acyl halide or an activated ester reacts with the hydroxyl groups on AR-5-1, AR-5-2 including the 12, 13-dihydro-12, 13-desepoxy or derivatives thereof. The pharmaceutically acceptable esters contemplated herein are in general those bearing acyl groups derived from the acids set forth above.

As used herein, the term alkanoyl refers to acyl groups derived from acids such as acetic, propionic, oxalic, oleic, palmitic, stearic, lauric, valeric, benzoic, adamantane carboxylic, fumaric and the like.

As used herein the term alkyl refers to straight or branched chain hydrocarbon radicals of from 1 to 18 carbon atoms, the preferred alkyl radicals being those having 1 to 8 carbon atoms.

The term aryl means phenyl and phenyl substituted by halogeno, trifluoromethyl, hydroxy and lower alkoxy.

The term aralkyl denotes aryl having an alkyl substituent wherein the aralkyl group has from 7 to 18 carbon atoms.

The term amino acid residue, as used herein contemplates D,L or DL-amino acid residues and includes but is not limited to alanyl, glycyl, argeninyl, sarcosyl, tyrosyl, phenylalanyl, methionyl, seryl, lysyl, asparaginyl, isoleucyl, leucyl, threonyl, histidyl, aspartyl, valyl, prolyl, glutaminyl, triptophanyl and glutamyl. It is to be understood that the amino group of such acids becomes the —NZ moiety defined for Q.

In the definition of R" and R'", the term "heterocycle wherein the hetero atom is selected from the group consisting of sulfur, nitrogen and oxygen", applicants contemplate such heterocycle radicals as pyridyl, furanyl, pyrrolidinyl, piperazinyl, pyrazinyl, azetidinyl, tetrazole, triazole, oxazole; isoxazole and the like.

The compounds of this invention can be regarded as several chemical types (a) the 9($\alpha,\beta$)-dihydro series (b) the 11($\alpha,\beta$)-amino series (c) the 11($\alpha,\beta$)-thio series and (d) the 4"-substituted series, each of which can contain the variations from the other chemical series.

The reaction sequences described hereinbelow are operable for preparing derivatives of both Antibiotic AR-5 component 1 and Antibiotic AR-5 component 2, unless the contrary is expressly stated. These antibiotics are quite often referred to as AR-5-1 and AR-5-2.

In order to prepare the compounds of this invention having a hydroxyl function at the 9-position, i.e., the 9-($\alpha,\beta$-dihydro derivative) AR-5-1 or AR-5-2 or a suitable derivatives thereof is treated with a reducing agent, such as sodium borohydride in a non-reactive solvent such as an alcohol (e.g. methanol). The resulting compound may be acylated with a conventional acylating agent such an acyl anhydride under conditions generally used in the art. The 2',4"-hydroxyl functions, if unacylated, will also esterify to produce a 9($\alpha,\beta$) 2'4"-triester. The 2'-acyl function may be removed by solvolysis, preferably using an alcohol (e.g. methanol) as the solvolyzing agent. The reduction-solvolysis sequence is obviously inoperable in those instances wherein the 4"-position is derivatized by a functional group which also reduces under the conditions described above. In such instances, it is advisable to obtain the desired product by reversing the steps in the sequence by derivatizing the 4"-position after the reduction and the solvolysis.

To prepare those derivatives wherein Q is a cyclic or acyclic secondary amino group, AR-5-1 or AR-5-2 is dissolved in the amine and the reaction is allowed to proceed from about 24 to about 72 hours. The 11-amino derivative is isolated by methods generally known in the art.

Alkylation and acylation of the 11-amine may be effected by methods generally used in the art. However, in the case of acylation, the 2' and 4" hydroxyl groups will also acylate. In order to obtain the free 2',4"-diol, the product must be subjected to selective hydrolysis by methods which take advantage of the greater stability to hydrolysis of acylamines than acylated alcohols.

The 11-amino group may be alklyated by conventional methods such as by treating the amine with an aldehyde or ketone in the presence of sodium cyanoborohydride. This reductive alkylation procedure also reduces the 9-ketone to the 9-($\alpha,\beta$)-dihydro derivative. Alkylation may also be effected by reacting the amine with a pyruvic acid analog of the formula R"CO—COOR". This reaction is also effected by the use of sodium cyanoborohydride and also results in the reduction of the 9-ketone to the 9-($\alpha,\beta$)dihydro derivative. The reaction is an excellent one for preparing compounds from which a reactive carboxylic acid group can be generated.

Alternatively, compounds of the latter type may be prepared directly from AR-5-1 or AR-5-2 by reacting with an amino acid in a non-reactive solvent such as a lower alcohol e.g. methanol or a cyclic ether e.g. tetrahydrofuran and dialkylacylamides, preferably dimethyl-formamide. The reaction is usually effected by the use of a salt of the amino acid and its esters in the presence of a slight excess of a tertiary base such as triethylamine.

Under substantially the same reaction conditions described immediately above, the derivatives wherein Q is SZ' may be prepared directly from AR-5-1 or AR-5-2. The reaction is an excellent method for preparing derivatives of sulfur containing amino acids such as cysteine, homocysteine, penicillamine and glutathione.

An alternate process for preparing the SZ" derivatives is by reacting AR-5-1 or AR-5-2 with a nucleophile such as an alkyl, aryl or aralkyl mercaptan such as an ethyl, butyl, phenethyl, p-methoxy-benzyl mercaptans. The reaction conditions are substantially the same as those described for the direct amination of the respective antibiotics. This process is an excellent one for preparing derivatives wherein the mercaptan reactant is readily available or wherein the mercaptan reactant is easily prepared.

The reactions described hereinbelow are operable for AR-5-1 and AR-5-2.

The compounds wherein X and Y are oxygen may be prepared by selectively esterifying the 2'-hydroxyl function by procedures known in the art, preferably by utilizing an acyl anhydride in acetone. The 2'-monoester derivative is then treated with an oxidizing agent such as dimethylsulfoxide, dicyclohexylcarbodiimide (DCC) and in a mixture of trifluoroacetic acid (TFA) and pyridine and benzene. This procedure is known in the art as the Moffatt oxidation. The 4"-keto derivative may be reacted with primary amines to form Schiff bases and with hydrazines to form hydrazones. The 4"-keto-derivative may be subjected to reduction by art recognized methods to yield the 9($\alpha,\beta$)-dihydro-4"-hydroxy derivative of the starting material in addition to the epimeric 4"-hydroxy compound. An excellent reagent with which to effect the reduction is lithium tri-tertiary butoxy aluminum hydride, LiA/H[OC(CH$_3$)$_3$]$_3$ preferably in a non-reactive solvent such as tetrahydrofuran. The 9-ketone may be regenerated by oxidation with manganese dioxide by the usual procedure. The resulting mixture of 4"-hydroxy epimers may be separated by the usual means such as chromatography on a suitable absorbent. Alternatively, the mixture may be subjected to solvolysis of the 2'-ester in a lower alcohol (e.g. methanol) and the resulting 2',4"-(α,β)-diol mixture separated.

In an alternative process, the 2'-ester derivative of the starting material (e.g. Antibiotics AR-5 component 1) may be mesylated at the 4"-position followed by treatment with sodium acetate in acetic acid as described by S. Winstein, et al, JACS, 83, 3235, 3244 (1961). The resulting 4"-acetate is epimeric to that in the starting materials and upon hydrolysis under basic conditions will yield the corresponding alcohols.

The 2'-acyloxy-4"-mesylates are also excellent intermediates for the preparation of 4"-halogeno derivatives of the Antibiotic AR-5 components. These 4"-halogeno derivatives are obtained by treating the 4"-mesylate with an alkali metal halide, preferably an iodide, in a non-reactive solvent such as acetone. The 4"-halogeno derivatives are formed with inversion and are, therefore, in the opposite configuration from the hydroxyl groups of the Antibiotic AR-5 compounds obtained from the fermentation.

Reduction of the resulting 4"-halogeno derivative under standard dehalogenating conditions, such as treating with tributyl tin hydride ($Bu_3SnH$) is a facile method for obtaining the 2'-acyloxyl-4"-deoxy Antibiotic AR-5 derivatives. Solvolysis of these compounds in a lower alcohol (methanol) affords the 2'-hydroxy-4"-deoxy derivative.

The 4" deoxy 4"-epi-azides of the Antibiotic AR-5 components may be prepared by treatment of the 4"-mesylate with sodium azide and may be converted to isocyanates and isothiocyanates by reaction with triphenylphosphine and carbon dioxide or triphenylphosphine and carbon disulfide, respectively.

The 4"-amines of the Antibiotic AR-5 components may be prepared directly from the 2"-acyloxy-4"-azides by reaction with triphenylphosphine by the procedure of H. Hellman et al, Chem. Ber. 89 2433 (1956). The 2'-acyl function may be removed by solvolysis as previously described. The 4"-epi-amines obtained by this procedure have a conformation which is opposite to that of the 4"-hydroxy function of the Antibiotic AR-5 components produced in the fermentation.

The 2'-acyloxy-4"-epi-amines of the Antibiotics AR-5 components may be used to prepare numerous other useful antibacterial derivatives. For example, by procedures generally known in the art, these compounds may be converted to such 4"-epi-derivatives as hydrazones, Schiff bases, urethanes including those derived from methyl, ethyl, phenyl and benzyl chloroformate (i.e. alkyl, aryl or aralkyl chloroformates).

The 2'-acyloxy-4"-epi-amines of the Antibiotic AR-5 components may also be used to prepare antibacterial amidines, guanidines, amides, alkoxyalkyl, hydroxyalkyl, alkyl, dialkyl, aryl, aralkyl and 3 to 7 membered heterocyclic derivatives wherein the hetero atoms are members selected from the group consisting of oxygen, nitrogen and sulfur. The procedures for the preparation of these amine derivatives are generally known in the art.

The 2'-acyloxy-4"-amines of the Antibiotic AR-5 components wherein the 4"-amino function has the same stereochemistry as the 4"-hydroxy compounds obtained from the fermentation may be prepared by treating the corresponding halogeno (iodo) derivative with hexamethylene tetramine by procedures generally known in the art. The 2'-acyloxy-4"-amines produced in this manner may also be used to produce the 4"-analogs of the antibacterially active compounds set forth above. However, the configuration at the 4"-position will be the same as the antibiotics produced in the fermentation.

The above-described reaction sequences are set forth in the following flow diagrams wherein the first 24 are operable for AR-5-1 and AR-5-2 and the remainder, except the preparation of compound 43 from compound 2, are operable for all of the AR-5 components. However, it is to be understood that the specific reagents and reactants used therein are illustrative and are not to be construed as limiting.

The following reaction sequences illustrate procedures for preparing the compounds of this invention of which the following are exemplary: 10,11-Dihydro-11(α,β)-amino AR-5-1; 10,11-Dihydro-11(α,β)-amino AR-5-2; 10,11-Dihydro-11(α,β)-(4-ethyl-2,3 dioxo-piperazinocarbonylamino) AR-5-1; 10,11-Dihydro-11(α,β)-(4-ethyl-2,3 dioxopiperazinocarbonylamino) AR-5-2; 9,10,11(α,β)-Tetrahydro-11(α,β)-(4-ethyl-2,3-dioxo-Piperazinocarbonylamino) AR-5-1; 9,10,11(α,β)-Tetrahydro-11(α,β)-(4-ethyl-2,3-dioxo-Piperazinocarbonylamino) AR-5-2; 10,11-Dihydro-11(α,β) (P-methoxybenzylthio) AR-5-1; 10,11-Dihydro-11(α,β) (P-methoxybenzylthio) AR-5-2; 10,11-Dihydro-11(α,β) (ethylthioxanthyl) AR-5-1; 10,11-Dihydro-11(α,β) (ethylthioxanthyl) AR-5-2; 10,11-Dihydro-11(α,β) (penicillaminyl) AR-5-1; 10,11-Dihydro-11(α,β) (penicillaminyl) AR-5-2; 10,11-Dihydro-11(α,β) (cysteinyl) AR-5-1 and 10,11-Dihydro-11(α,β) (cysteinyl) AR-5-2.

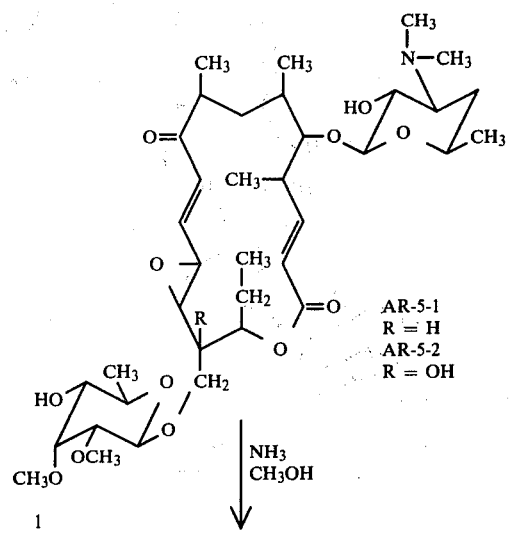

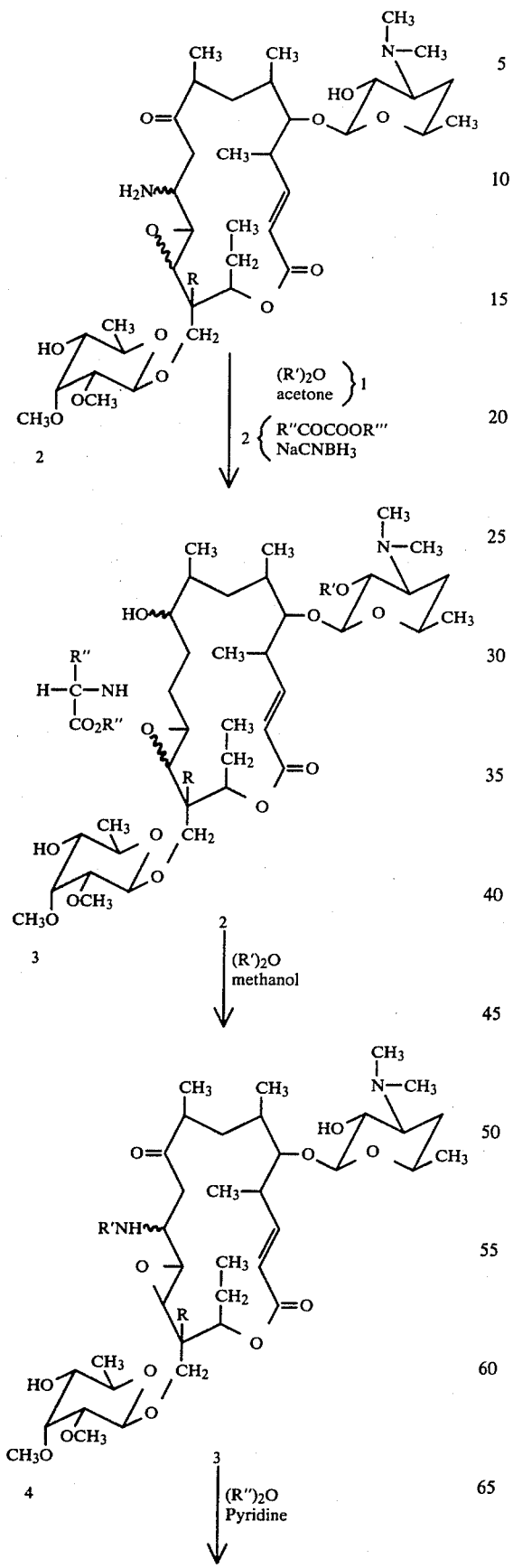
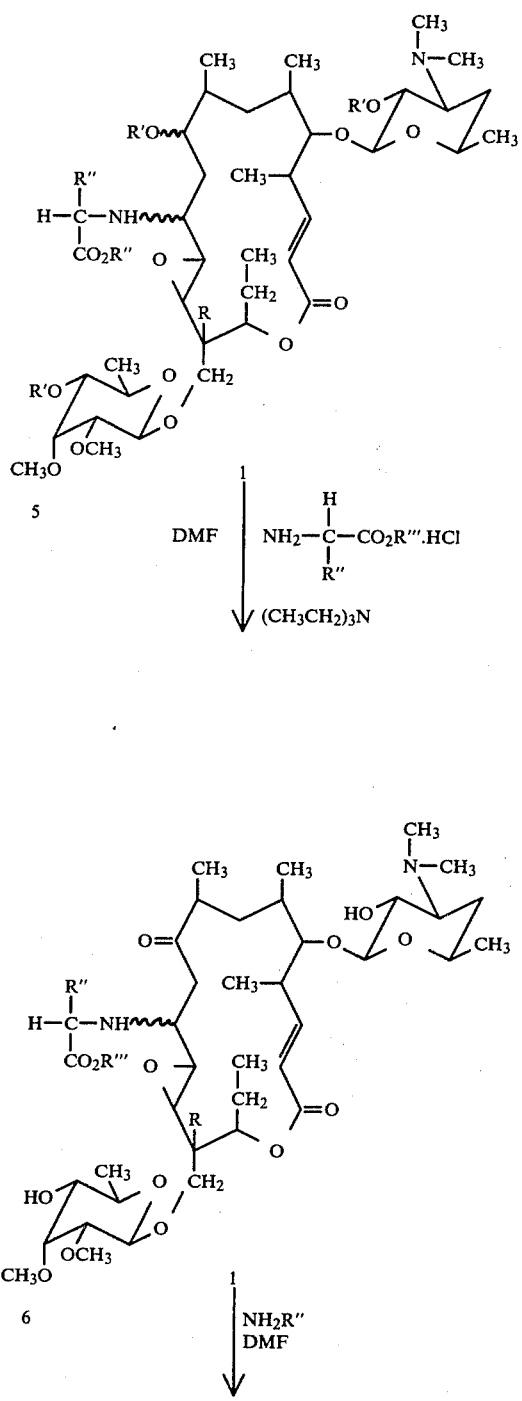

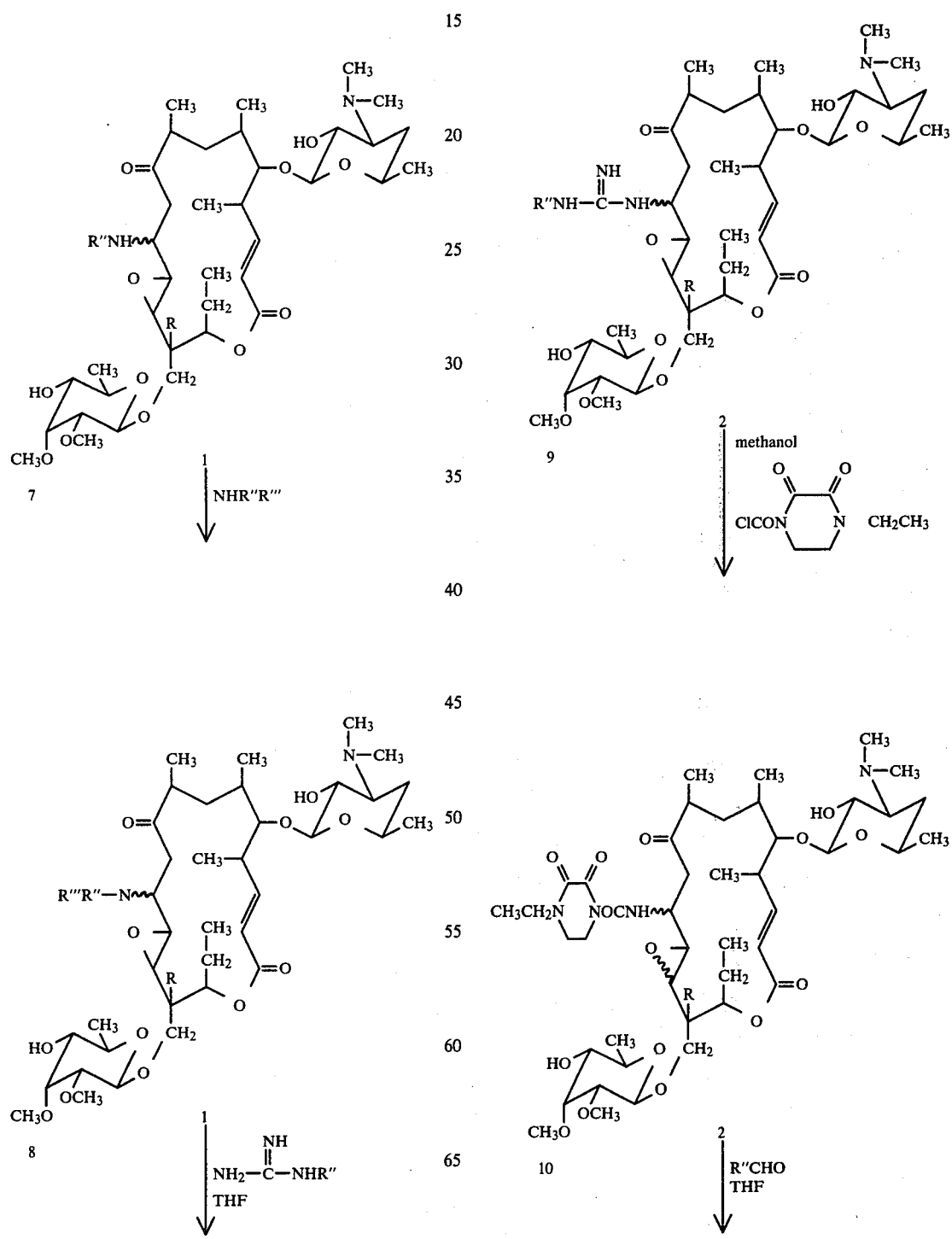

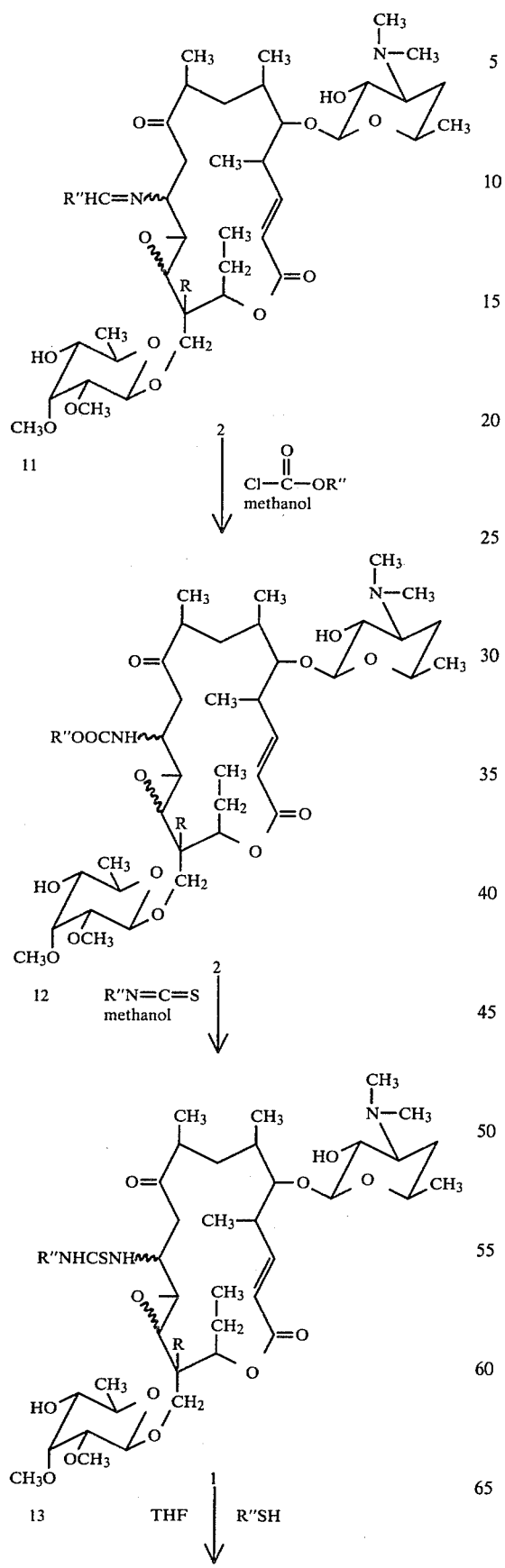
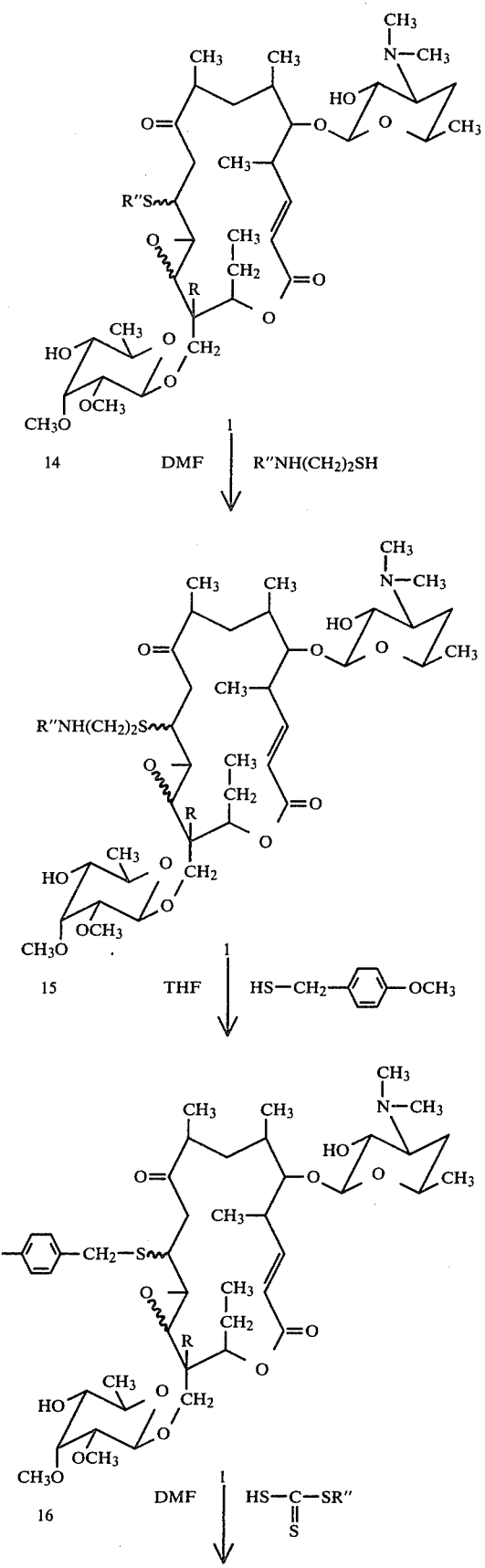

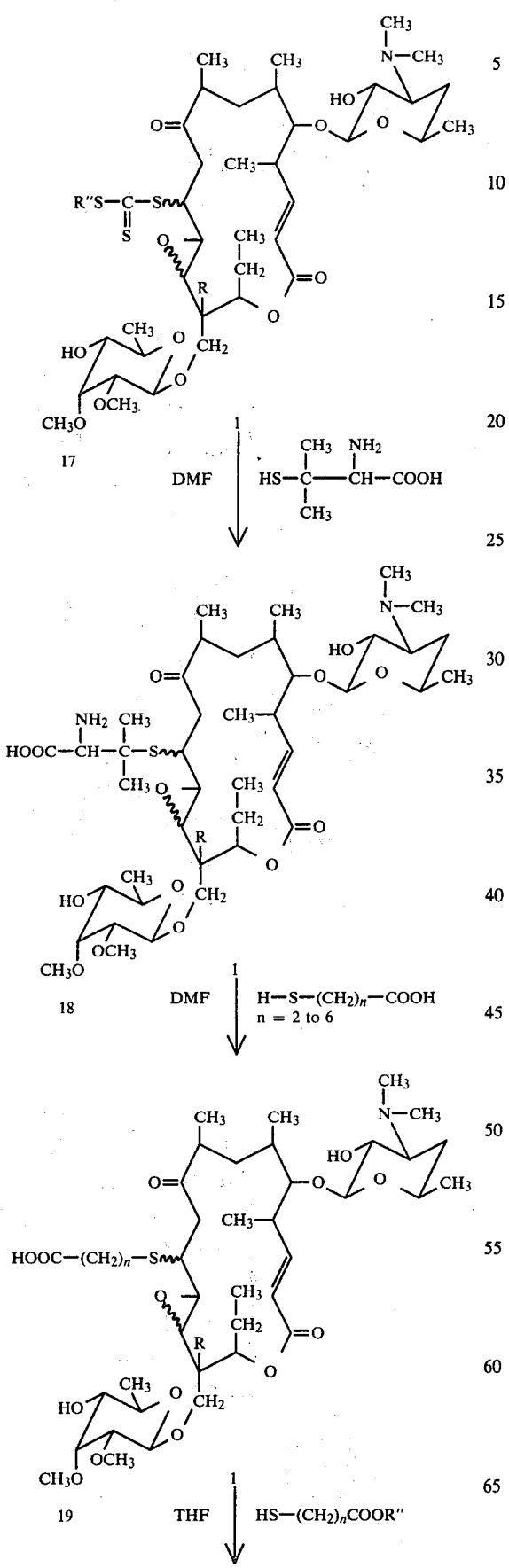

-continued
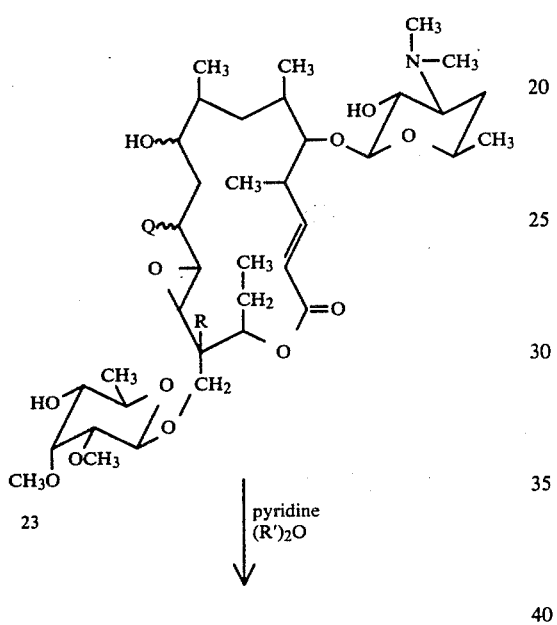
23
↓ pyridine (R')₂O
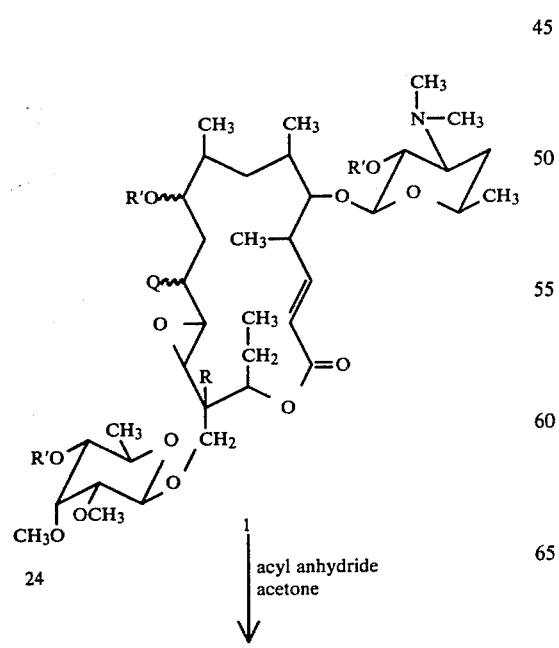
24
↓ acyl anhydride acetone
-continued
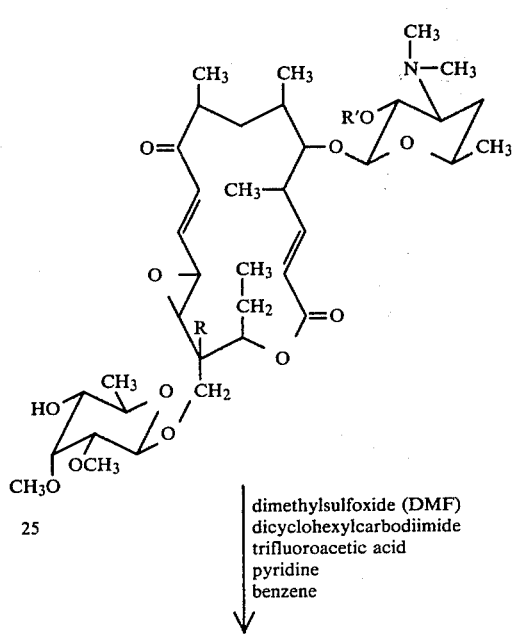
25
↓ dimethylsulfoxide (DMF)
dicyclohexylcarbodiimide
trifluoroacetic acid
pyridine
benzene
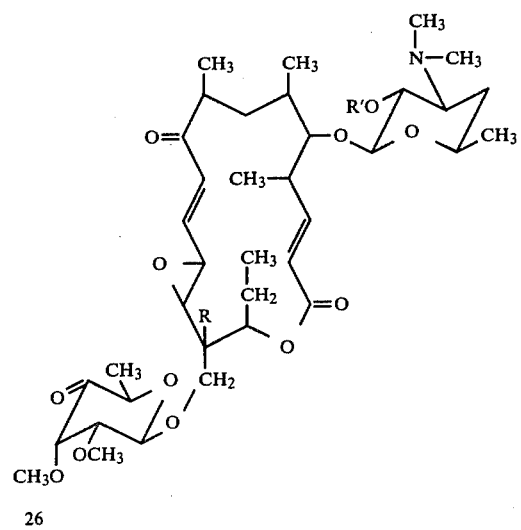
26

-continued
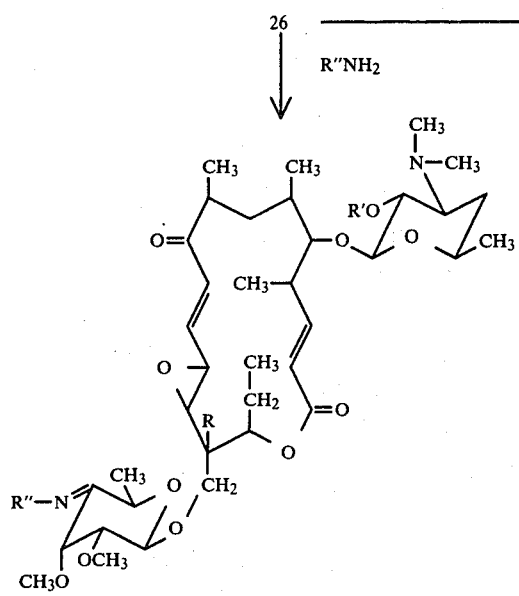
27
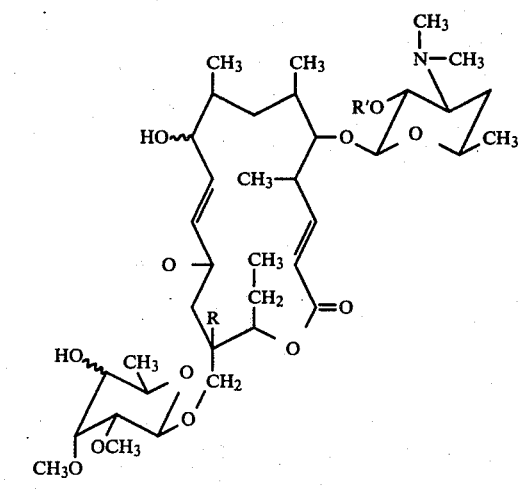
29
↓ R″NH₂ (from 26 to 27)
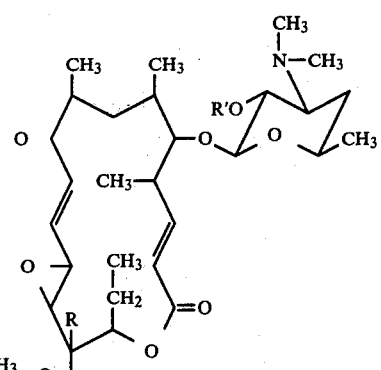
28
↓ MnO₂
30
↓ LiAlH[OC(CH₃)₃]₃ THF  26
← R″—NH—NH₂

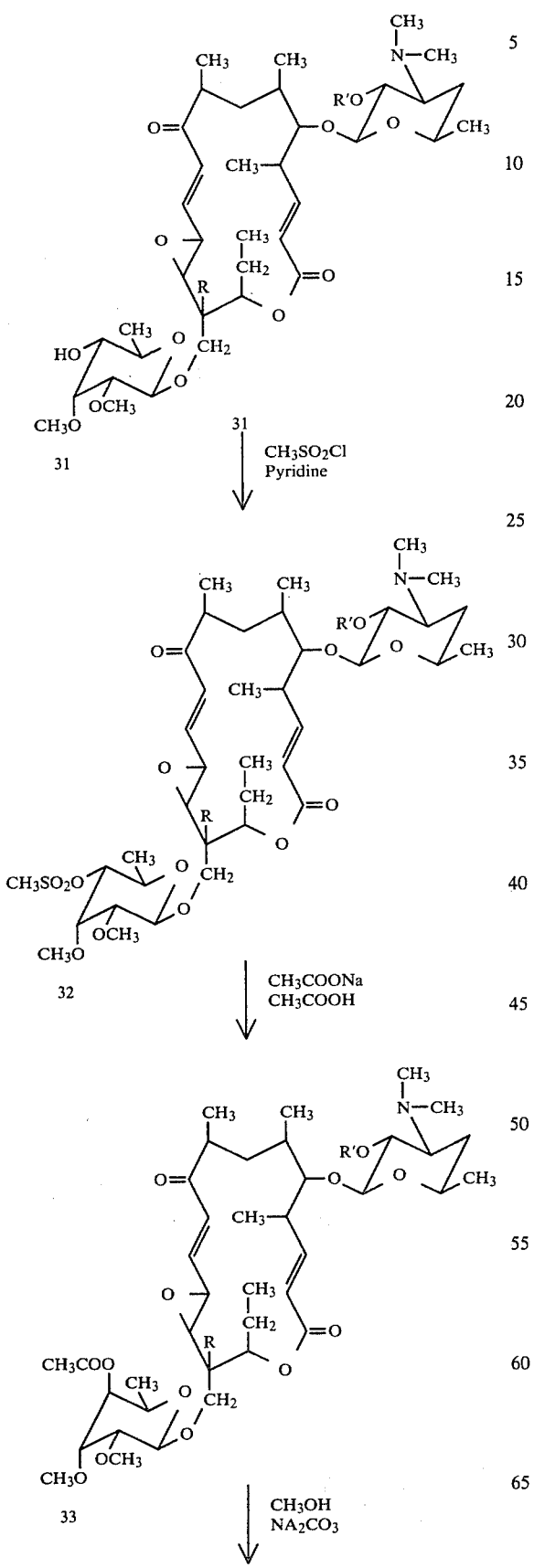
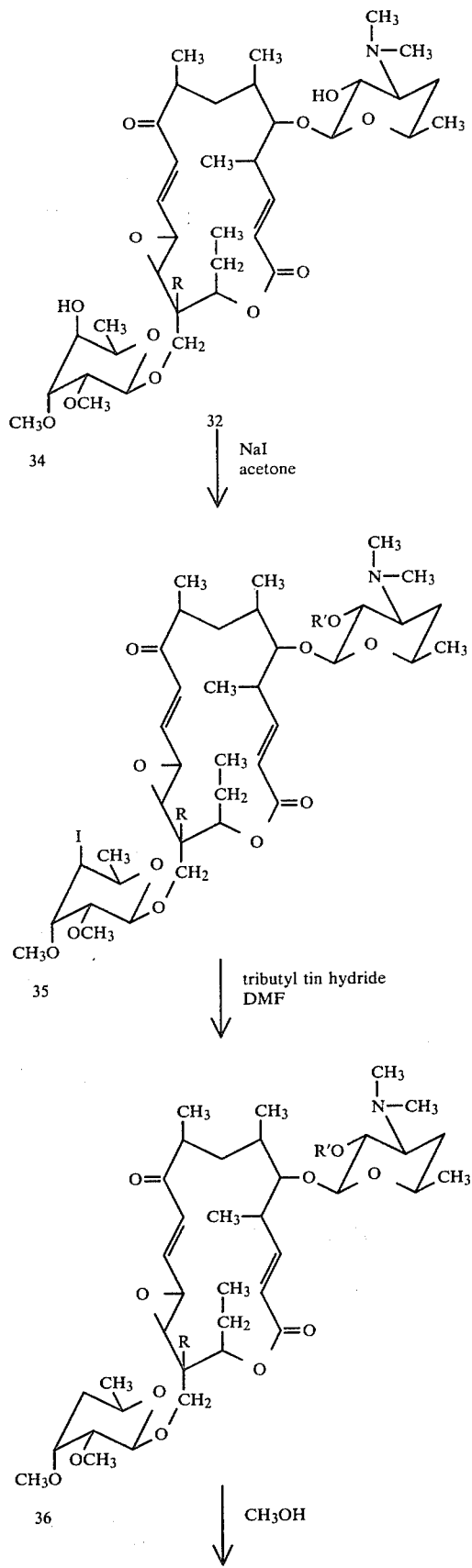

-continued
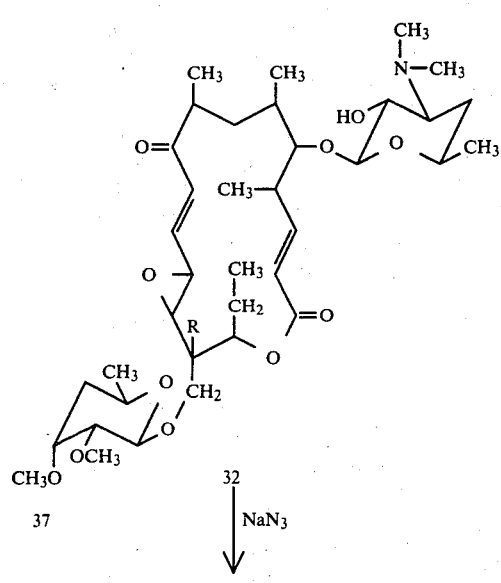
37
↓ NaN₃ 32
-continued
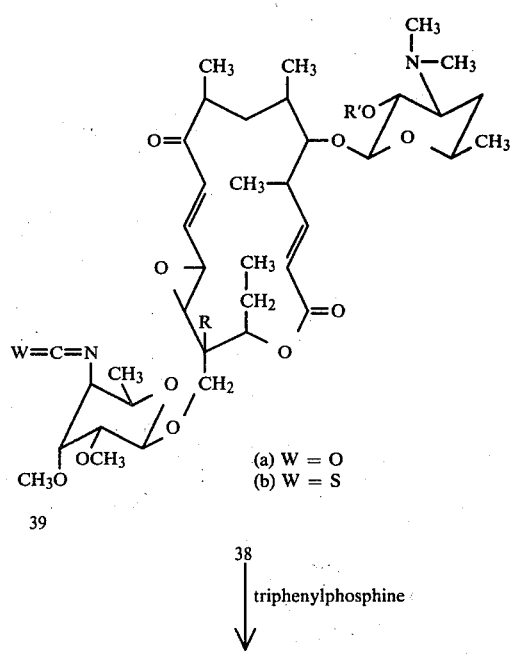
39 (a) W = O
(b) W = S
↓ triphenylphosphine 38
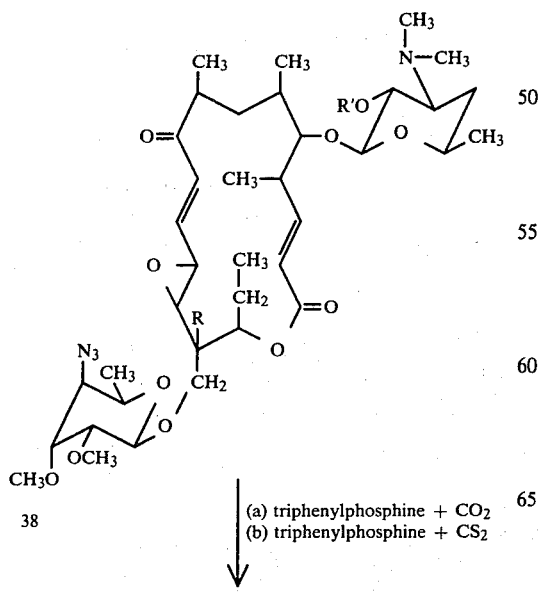
38
↓ (a) triphenylphosphine + CO₂
(b) triphenylphosphine + CS₂
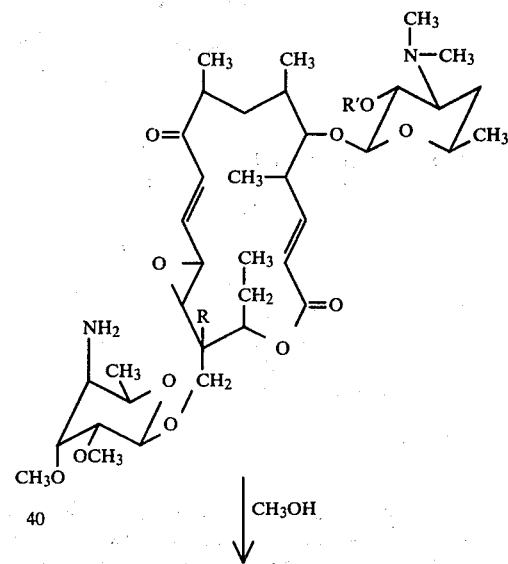
40
↓ CH₃OH

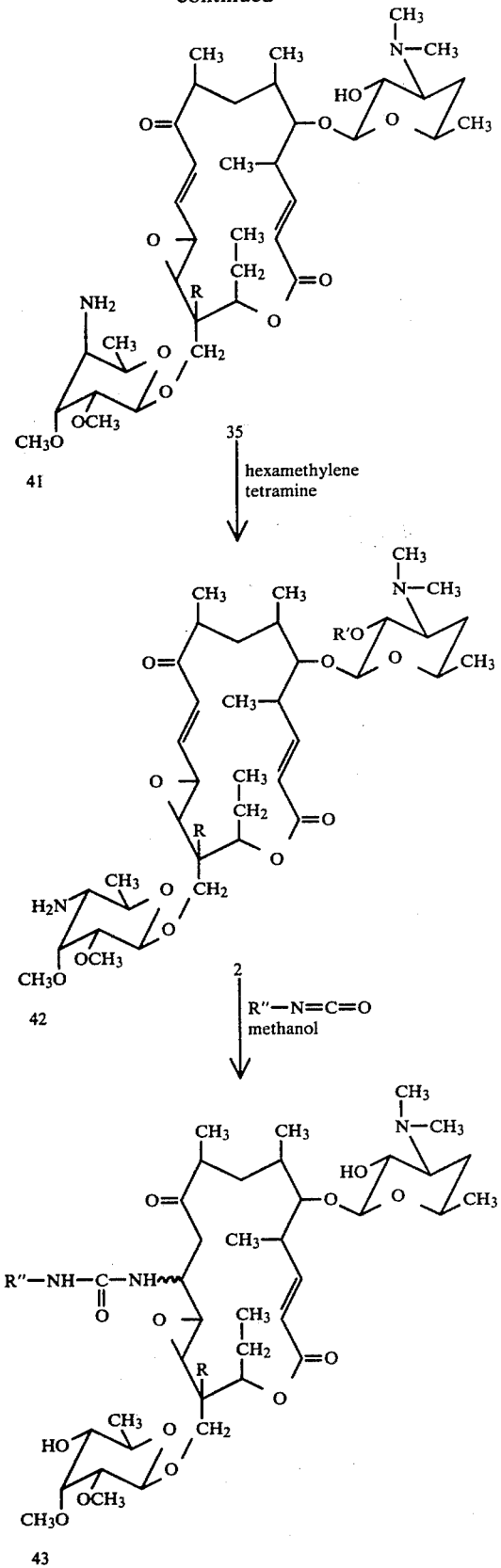

bacteria. Exemplary of the bacteria against which the compounds of this invention are active are various strains of *Streptococcus pyogenes*, *Staphylococcus aureus* and *Bacillus subtilis*.

Of course, it should be appreciated that the amount of antibacterial derivative used will vary dependent upon the particular compound used, the mode of application, the route of administration and the like. The factors which modify the action of the drug will be taken into account by the skilled practitioner. For example, age body weight, sex, diet, time of administration, route of administration, rate of metabolism or excretion, other drugs being administered, severity of infection all play a role in the quantum and frequency of administration of the derivatives disclosed herein. However, the compounds of this invention are generally administered in the range of from about 5 to about 50 mg/kg/day in divided doses.

The antibacterial compounds of this invention may be administered in the form of non-toxic pharmaceutically acceptable acid addition salts, such as those set forth hereinabove. They may also be in the form of nontoxic pharmaceutical esters or of salts of such esters.

The antibacterial compounds of this invention may be dispensed in the form of capsules, tablets, elixirs and as injectable solutions and suspensions. Each of these dosage forms may also contain the excipients generally used in the art such as those set forth in U.S. Pat. No. 4,056,616.

EXAMPLE 1

10,11-Dihydro-11($\alpha,\beta$)(amino)-AR-5-1

Dissolve 3.5 g of AR-5-1 in 35 mol of methanol saturated with ammonia. Stir the solution at room temperature (20° C.) for 2 days and concentrate the solution to a residue. Dissolve the residue in a solvent system consisting of toluene, methylene chloride, methanol and concentrated ammonium hydroxide in the ratio of 16:4:1:1 and chromatograph on a silica gel column containing 400 g of silica gel using the above described solvent system as eluant. Combine and concentrate the fractions containing antibiotic to a residue.

| Yield - 1.45g Elemental analysis | | |
|---|---|---|
| | Calc. | Found |
| C = | 59.65% | 59.39% |
| H = | 8.66% | 8.97% |
| N = | 3.76% | 3.62% |

In a similar manner, by substituting an equivalent quantity of AR-5-2 and by following the process of this Example 10,11-dihydro-11($\alpha,\beta$)amino AR-5-2 may be prepared.

EXAMPLE 2

10,11-Dihydro-11($\alpha,\beta$)(p-methoxybenzylthio)AR-5-2

Dissolve 100 mg of AR-5-2 just enough tetrahydrofuran to dissolve it. Add 3 drops of p-methoxybenzythiol and allow the solution to stand at room temperature (20°) for about 72 hours. Dilute the reaction mixture with ethyl acetate. Chromatograph on silica gel GF. Ⓐ preparative plates 1000$\mu$ thick using as the developing solution chloroform: methanol: petroleum ether: water in the ratio of 3:3:1:1. Remove the silica gel containing antibiotic, as determined by observing under ultraviolet light, and dissolve the product in ethyl acetate. Concentrate the ethyl acetate extract to a residue to obtain thereby 34 mg of AR-5-2. Extract the silica gel with acetone and concentrate to a residue yield-44 mg of the product of this example.

By substituting an equivalent quantity of AR-5-1 and following the process of this Example 10,11-dihydro11-(α,β)(p-methoxybenzylthio) AR-5-1 may be obtained.

In a similar manner, by substituting an equivalent quantity of other thiols and by following the process of this 11(α,β)thio of AR-5-1 or AR-5-2 may be prepared. Examples of such thio derivatives are set forth in the reaction sequences herein above.

EXAMPLE 3

11-(α,β) (Piperidino)-10,11-Dihydro AR-5-2

Dissolve 500 mg of AR-5-2 in 3 ml of freshly distilled piperidine under a nitrogen atmosphere in an ice bath. Allow the reaction mixture to warm to room temperature, then stir overnight under nitrogen. Remove the solvent in vacuo and triturate the residue with hexane. Collect the solids by filtration, wash well with hexane and dry to obtain the product of this example.

In a similar manner, by using an equivalent quantity of AR-5-2 and an equivalent quantity of morpholine or N-methyl piperazine or thiomorpholine or the like and by following the process of Example 3, the following compounds may be prepared:

11-(α,β) (morpholino)-10,11-dihydro AR-5-2.
11-(α,β) (N-methylpiperazino)-10,11-dihydro AR-5-B 2, and
11-(α,β) (thiomorpholino)-10,11-dihydro AR-5-2.

Further, by substituting AR-5-1 for AR-5-2 and by following the process of this example, the corresponding AR-5-1 derivatives may be prepared.

We claim:
1. Compounds of the formulae:

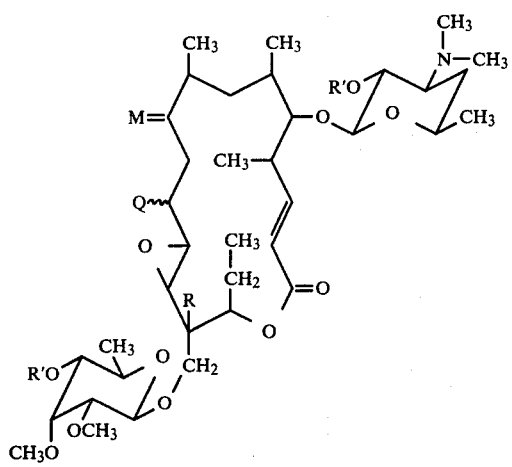

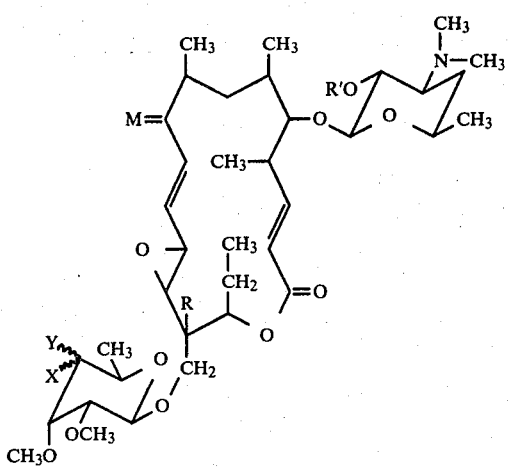

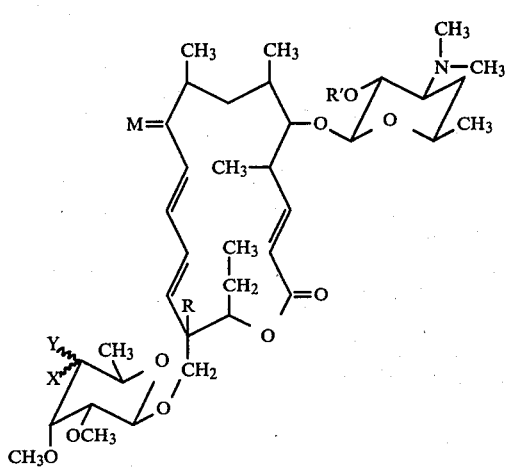

and the pharmaceutically acceptable salts thereof and esters thereof of acids selected from the group consisting of acetic, propionic, oxalic, valeric, oleic, palmitic, stearic, lauric, benzoic, lactic, para toluene sulfonic, methane sulfonic, citric, maleic, fumaric, tartaric, succinic, naphthalene sulfonic and adamantoic, wherein the wavy line indicates that the substituent may be in any of the possible stereochemical configurations; R is a member of a group consisting of hydrogen and hydroxyl; R' is a member of a group consisting of hydrogen and $C_2-C_{18}$ alkanoyl, carbamoyl and thiocarbamoyl; M is a member of the group consisting of oxygen and H,OR'; Q is a member of the group consisting of —NZ and —SZ' wherein —NZ is a member of the group consisting of amino, acylamino wherein the acyl group is an amionacid residue, $C_1-C_{18}$ akylamino, $C_2-C_{36}$ dialkylamino, hydroxy $(C_1-C_{18})$alkylamino, $C_1-C_{18}$ alkylimino, or $C_7-C_{18}$ aralkylimino, aminothiocarbonylamino$(C_1-C_{18})$alkyl, amidinyl, $C_1-C_{18}$ alkylcarboxyamino, ureido, 4-ethyl-2,3-dioxopiperazinocarbonylamino, guanidino, $C_1-C_{18}$, alkylguanidino and an aminoacid residue; —SZ' is a member of the group consisting of $C_1-C_{18}$ alkylthio, thioxanthyl, including $C_1-C_{18}$ alkyl, phenyl, phenyl substituted with a member of the group consisting of halogeno, trifluoromethyl, hydroxy and lower alkoxy, $C_7-C_{18}$ aralkyl, thioxanthyl, $C_1-C_{18}$ alkylamino$(C_1-C_{18})$alkylthio, phenylthio, halogenophenylthio, trifluoromethylphenylthio, hydroxyphenylthio, loweralkoxyphenylthio, $C_2-C_{18}$ aralkylthio, heterocyclethio, heterocycle (C₁-C₁₈) alkylthio, heterocycle (C₇-C₁₈) aralkylthio, heterocyclephenylthio, heterocycle(halogeno) phenylthio, heterocycle(trifluoromethyl)phenylthio, heterocycle(hydroxy)phenylthio, heterocycle(loweralkoxy)phenylthio, (wherein the heterocycle contains at least one hetero atom selected from the group consisting of sulfur, nitrogen and oxygen), C₁-C₁₈ alkylcarboxy(C₁-C₁₈)alkylthio and sulfur containing amino acid residues, X is a member of the group consisting of hydrogen, OR'epi, mesyloxy, tosyloxy, trifluoromethanesulfonyloxy, halogeno, azido, amino, isocyanato, thiosiocyanato, C₁-C₁₈ alkylimino, phenylimino, halogenophenylimino, trifluoromethylphenylimino, hydroxyphenylimino, loweralkoxyphenylimino, C₇-C₁₈ aralkylimino, urethano, amidino, guanidino, C₁-C₁₈ alkoxyamino, cyclic-guanidino when Y is hydrogen; and Y in combination with X is oxygen.

2. A compound of claim 1 of the formula:

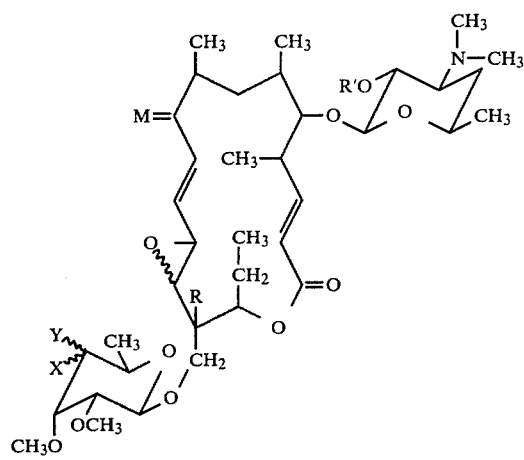

wherein R, R', M, X and Y are as defined in claim 1.

3. A compound of claim 1 of the formula:

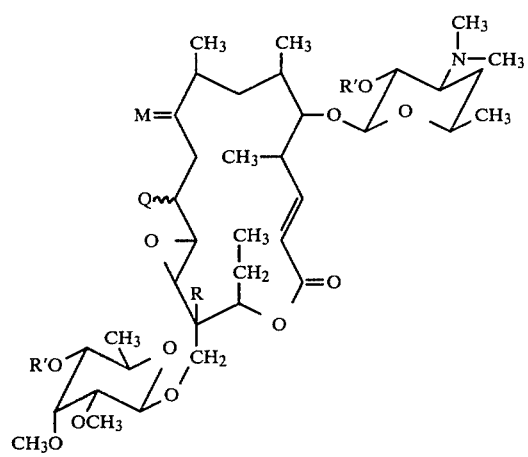

wherein R, R', M and Q are as defined in claim 1.

4. A compound of claim 3 wherein R, R', and M are as defined in said claim 3 and Q is —NZ.

5. A compound of claim 3 wherein R, R' and M are as defined in said claim 3 and Q is —SZ.

6. A compound of claim 4 wherein R, R' and Q are as defined in said claim 4 and M is oxygen.

7. A compound of claim 6 wherein R and R' are hydrogen and Q is —NH₂, said compound being 10,11-dihydro-11(α,β)-amino AR-5-1.

8. A compound of claim 6 wherein R is hydroxyl, R' is hydrogen and Q is —NH₂, said compound being 10,11-dihydro-11(α,β)-amino AR-5-2.

9. A compound of claim 4 wherein R, R' and Q are as defined in said claim 4 and M is H,OR'.

10. A compound of claim 9 wherein R and R' are hydrogen and Q is

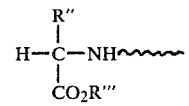

wherein R'' and R''' which may be the same or different are members of the group consisting of C₁-C₁₈ alkyl, C₇-C₁₈ aralkyl and 3 to 7 membered heterocycles wherein the hetero atoms are selected from the group consisting of sulfur, nitrogen and oxygen.

11. A compound of claim 6 wherein R and R' are hydrogen and Q is

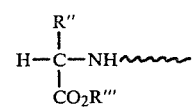

wherein R'' and R''' which may be the same or different are members of the group consisting of C₁-C₁₈ alkyl, C₇-C₁₈ aralkyl and 3 to 7 membered heterocycles wherein the hetero atoms are selected from the group consisting of sulfur, nitrogen and oxygen.

12. A compound of claim 6 wherein R and R' are hydrogen and Q is alkylamino.

13. A compound of claim 6 wherein R is hydroxyl, R' is hydrogen and Q is alkylamino.

14. A compound of claim 6 wherein R and R' are hydrogen and Q is 4-ethyl-2,3-dioxo-piperazinocarbonylamino, said compound being 10,11-dihydro-11(α,β)-(4-ethyl-2,3-dioxo-piperazinocarbonylamino) AR-5-1.

15. A compound of claim 6 wherein R is hydroxyl, R' is hydrogen and Q is 4-ethyl-2,3-dioxo-piperazinocarbonylamino, said compound being 10,11-dihydro-11(α,β)-(4-ethyl-2,3-dioxo-piperazinocarbonylamino) AR-5-2.

16. A compound of claim 9 wherein R and R' are hydrogen and Q is 4-ethyl-2,3-dioxo-piperazinocarbonylamino, said compound being 9,10,11(α,β) tetrahydro-11 (α,β)-(4-ethyl-2,3-dioxo-piperazinocarbonylamino) AR-5-1.

17. A compound of claim 9 wherein R is hydroxyl, R' is hydrogen and Q is 4-ethyl-2,3-dioxo-piperazinocarbonylamino, said compound being 9,10,11(α,β)-tetrahydro 11 (α,β)-(4-ethyl-2,3-dioxo-piperazinocarbonylamino) AR-5-2.

18. A compound of claim 6 wherein R and R' are hydrogen and Q is

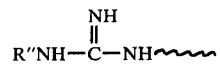

wherein R'' is selected from the group consisting of C₁-C₁₈ alkyl, C₇-C₁₈ aralkyl and 3 to 7 membered heterocycles wherein the hetero atoms are selected from the group consisting of sulfur, nitrogen and oxygen.

19. A compound of claim 6 wherein R is hydroxyl R' is hydrogen and Q is

wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

20. A compound of claim 6 wherein R and R' are hydrogen and Q is

wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

21. A compound of claim 6 wherein R is hydroxyl, R' is hydrogen and Q is

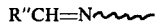

wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

22. A compound of claim 6 wherein R and R' are hydrogen and Q is

wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

23. A compound of claim 6 wherein R is hydroxyl, R' is hydrogen and Q is

wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

24. A compound of claim 6 wherein R and R' are hydrogen and Q is R″NHCSNH∼∼ wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

25. A compound of claim 6 wherein R is hydroxyl, R' is hydrogen and Q is R″NHCSNH∼∼ wherein R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

26. A compound of claim 5 wherein R and R' are hydrogen, Q is as defined in said claim 5 and M is oxygen.

27. A compound of claim 5 wherein R is hydroxyl, R' is hydrogen, Q is as defined in said claim 5 and M is oxygen.

28. A compound of claim 5 wherein R and R' are hydrogen, Q is as defined in said claim 5 and M is H,OR'.

29. A compound of claim 5 wherein R is hydroxyl, R' is hydrogen, Q is as defined in said claim 5 and M is H,OR'.

30. A compound of claim 26 wherein W is R″S∼∼ and R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

31. A compound of claim 27 wherein Q is R″S∼∼ and R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

32. A compound of claim 26 wherein Q is R″NH(CH$_2$)$_2$S∼∼ and R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

33. A compound of claim 27 wherein Q is R″NH(CH$_2$)$_2$S∼∼ and R″ is selected from the group consisting of $C_1$-$C_{18}$ alkyl, $C_7$-$C_{18}$ aralkyl and 3 to 7 membered heterocycles wherein the hetero atoms are selected from the group consisting of sulfur, nitrogen and oxygen.

34. A compound of claim 26 wherein Q is

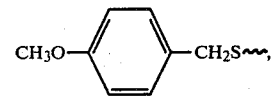

said compound being 10,11-dihydro-11($\alpha,\beta$) (p methoxybenzylthio) AR-5-1.

35. A compound of claim 27 wherein Q is

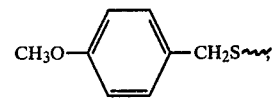

said compound being 10,11-dihydro-11($\alpha,\beta$) (p methoxybenzylthio) AR-5-2.

36. A compound of claim 26 wherein Q is

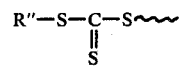

and R″ is ethyl, said compound being 10,11-dihydro-11($\alpha,\beta$)(ethylthioxanthyl) AR-5-1.

37. A compound of claim 27 wherein Q is

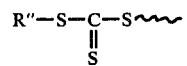

and R″ is ethyl, said compound being 10,11-dihydro-11($\alpha,\beta$) (ethylthioxanthyl) AR-5-2.

38. A compound of claim 26 wherein Q is

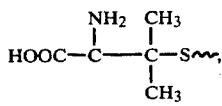

said compound being 10,11-dihydro-11(α,β)(penicillaminyl) AR-5-1.

39. A compound of claim 27 wherein Q is

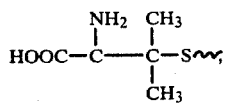

said compound being 10,11-dihydro-11(α,β)(penicillaminyl) AR-5-2.

40. A compound of claim 26 wherein Q is

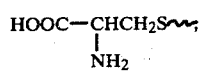

said compound being 10,11-dihydro-11(α,β)(cysteinyl) AR-5-1.

41. A compound of claim 27 wherein Q is

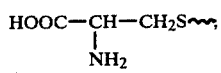

said compound being 10,11-dihydro-11(α,β)(cysteinyl) AR-5-2.

42. The compound of claim 40 wherein the Q substituent is selected from the group consisting of the D,L or DL form.

43. The compound of claim 41 wherein the Q substituent is selected from the group consisting of the D,L or DL form.

44. A compound of claim 1 of the formula:

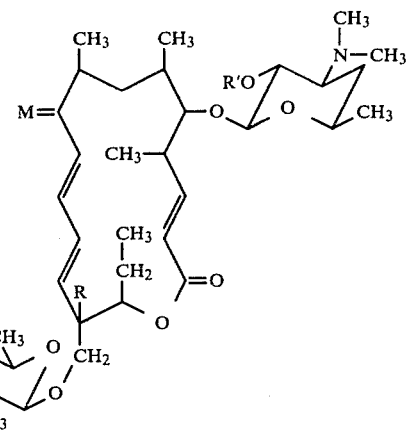

wherein R, R', M, X and Y are as defined in said claim 1.

45. A compound of claim 44 wherein R and R' are hydrogen; M, X and Y are as defined in said claim 44.

46. A compound of claim 44 wherein R is hydroxyl, R' is hydrogen M, X and Y are as defined in said claim 44.

47. A compound of claim 4 wherein R and R' are hydrogen, m is oxygen and Q is —NZ selected from the group consisting of piperidino, N-methyl piperazino, morpholino and thiomorpholino.

48. A compound of claim 4 wherein R is hydroxy, R' is hydrogen and Q is —NZ selected from the group consisting of piperidino, N-methyl piperazino, morpholino and thiomorpholino.

49. A compound of claim 47 wherein Q is piperidino, said compound being 11-(α,β) (piperidino)-10,11-dihydro AR-5-1.

50. A compound of claim 48 wherein Q is piperidino, said compound being 11-(α,β) (piperidino)-10,11-dihydro AR-5-2.

* * * * *